(12) United States Patent
Sato (10) Patent No.: US 10,803,335 B2
(45) Date of Patent: Oct. 13, 2020

(54) EMOTION ESTIMATING APPARATUS

(71) Applicant: KYUSHU INSTITUTE OF TECHNOLOGY, Kitakyushu-shi, Fukuoka (JP)

(72) Inventor: Yasushi Sato, Kitakyushu (JP)

(73) Assignee: KYUSHU INSTITUTE OF TECHNOLOGY, Kitakyushu-shi (JP)

( * ) Notice: Subject to any disclaimer, the term of this patent is extended or adjusted under 35 U.S.C. 154(b) by 0 days.

(21) Appl. No.: 16/497,846

(22) PCT Filed: Mar. 8, 2018

(86) PCT No.: PCT/JP2018/008943
§ 371 (c)(1),
(2) Date: Sep. 26, 2019

(87) PCT Pub. No.: WO2018/180330
PCT Pub. Date: Oct. 4, 2018

(65) Prior Publication Data
US 2020/0250446 A1    Aug. 6, 2020

(30) Foreign Application Priority Data

Mar. 28, 2017  (JP) .................................. 2017-063539

(51) Int. Cl.
G06K 9/00    (2006.01)
G06F 3/01    (2006.01)
A61B 5/18    (2006.01)

(52) U.S. Cl.
CPC ............ *G06K 9/00845* (2013.01); *A61B 5/18* (2013.01); *G06F 3/011* (2013.01)

(58) Field of Classification Search
None
See application file for complete search history.

(56) References Cited

U.S. PATENT DOCUMENTS

2003/0172043 A1* 9/2003 Guyon ................... G06N 20/00
                                                      706/48
2007/0038382 A1* 2/2007 Keenan ................ A61B 5/7203
                                                      702/19

(Continued)

FOREIGN PATENT DOCUMENTS

JP            6-86762    * 3/1994 .......... A61B 5/0476
JP        H11-128185 A     5/1999

(Continued)

*Primary Examiner* — Hung Q Dang
(74) *Attorney, Agent, or Firm* — Oliff PLC (57) ABSTRACT

Provided is an. emotion. estimating apparatus capable of precisely estimating an emotion and mental state of a measurement subject by using a non-contact pulse detection technology. The emotion estimating apparatus forcibly performs re-sampling processing of digital biometric data generated by converting a heart rate signal to digital data after extracting data for one cycle at an RR interval, and obtains coefficients of harmonic components by a DCT conversion processing unit. From the coefficients of the harmonic components, AC components are removed by LPFs, whereby a coefficient data array is obtained.. The coefficient data array is compared to a dictionary data group, in which dictionary data is a characteristic quantity indicating an emotion or mental state, and a similarity therebetween is calculated, whereby an emotion or mental state of a subject is estimated on the basis of the heart rate signal of the subject.

2 Claims, 5 Drawing Sheets

(56) References Cited

U.S. PATENT DOCUMENTS

| | | | |
|---|---|---|---|
| 2007/0192103 A1* | 8/2007 | Sato | G10L 25/78 704/253 |
| 2009/0043216 A1* | 2/2009 | Lin | A61B 5/0205 600/501 |
| 2009/0198147 A1 | 8/2009 | Ono et al. | |
| 2009/0275853 A1* | 11/2009 | Sarkela | A61B 5/04014 600/544 |
| 2011/0257536 A1* | 10/2011 | Ser | A61B 5/0816 600/484 |
| 2016/0354027 A1 | 12/2016 | Benson et al. | |
| 2018/0042499 A1 | 2/2018 | Sato | |
| 2018/0049660 A1* | 2/2018 | Sato | A61B 5/7203 |
| 2018/0296107 A1* | 10/2018 | Harrer | A61B 5/6803 |
| 2018/0368723 A1* | 12/2018 | Ibanez Catala | A61B 5/0432 |

FOREIGN PATENT DOCUMENTS

| | | |
|---|---|---|
| JP | 2009-178456 A | 8/2009 |
| JP | 2016-159081 A | 9/2016 |
| JP | 6083441 B2 | 2/2017 |
| WO | 2014/084162 A1 | 6/2014 |
| WO | 2015/127193 A1 | 8/2015 |

* cited by examiner

EMOTION ESTIMATING APPARATUS

TECHNICAL FIELD

The present invention relates to an emotion estimating apparatus that estimates a human emotion from a pulse signal.

BACKGROUND ART

Many business operators and engineers are developing a drowsy driving prevention system that detects a fatigue state of a driver driving a car and estimates a dangerous state early to issue a warning to the driver.

Patent Literature 1 discloses a vehicular occupant emotion correspondence control apparatus that estimates an emotion of a passenger from expression. and. a pulse of the passenger.

Patent Literature 2 discloses a biometric signal detection apparatus that detects a. pulse without contact,.

CITATION LIST

Patent Literature

Patent Literature 1: JP 6083441 B2
Patent Literature 2: JP 2016-159081 A

SUMMARY OF INVENTION cl Technical Problem

Technologies are known for detecting fatigue from a pulse.

A human pulse is about 1 Hz, but has a fluctuation of about 0.1 to 0.3 Hz. Components of this fluctuation can be extracted by performing Fourier transform to the human pulse.

It is known that a fluctuation component of 0.3 Hz is caused by human respiration. When a person inhales oxygen, the pulse rate of the heart becomes slightly faster due to an increase in the amount of the oxygen.

It is known that a fluctuation component of 0.1 Hz is caused by human blood pressure.

It is known that a human fatigue degree and tension state can be known when a magnitude relationship is analyzed between the fluctuation component of 0.3 Hz and the fluctuation component of 0.1 Hz.

However, to acquire the magnitude relationship between the fluctuation components, it is necessary to accurately acquire a pulse signal, as a premise.

A relatively accurate waveform can be obtained if it is an electrocardiographic waveform using an electrode closely attached to skin, but in the case of pulse acquisition using a medium such as a radio wave or light, a position (phase) on the time axis of the peak easily shifts. Then, the shift of the peak becomes a large noise to the fluctuation components, and it becomes difficult to accurately acquire the fluctuation components.

For this reason, in a fatigue degree measurement device and the like configured by such a conventional technology, reliability of the measurement result has been low. In other words, the reliability has been low of fatigue degree detection using pulse detection technology using a radio wave, and it has not been possible to implement precise estimation of an emotion. of a measurement subject, and eventually a drowsy driving prevention system, by only adopting the conventional technology as it is.

The present invention has been made in view of such problems, and it is an object of the present invention to provide an emotion estimating apparatus capable of precisely estimating an emotion and mental state of a. measurement subject by using a non-contact pulse detection technology.

Solution to Problem

To solve the above problems, an emotion estimating apparatus of the present invention includes: a re-sampling processing unit that extracts data for one cycle based on an RR interval from digital biometric data converted from a heart rate signal to digital data and converts the data to a predetermined number of samples; a DCT conversion processing unit that performs discrete cosine transform on normalized digital biometric data whose number of samples is fixed by the re-sampling processing unit; a low pass filter group that reduces an AC component for each coefficient data for a coefficient data array output from the DCT conversion processing unit; and an estimating processing unit that estimates a most similar emotion or mental state by comparing the coefficient data array obtained from the low pass filter group with a dictionary data group that is an aggregation of dictionary data created for each emotion or mental state.

Advantageous Effects of Invention

According to the present invention, the emotion estimating apparatus can be provided capable of precisely estimating an emotion and mental state of a measurement subject by using the non-contact pulse detection technology.

Problems, configurations, and effects other than. those described above will be apparent from the description of the embodiments below.

DESCRIPTION OF EMBODIMENTS

[Emotion Estimating Apparatus: Overview]

The inventor has abandoned a conventional method of acquiring fluctuation components from a pulse waveform, and has conceived of acquiring harmonic components from a normalized pulse waveform.

An actual human pulse waveform is followed by fine micro-vibration waveforms immediately before and after contraction of a ventricle in which an R wave is generated. These vibration waveforms have names such as P, Q, S, T, and the like.

Thus, when frequency analysis is performed including these micro-vibration waveforms, harmonic components with an RR interval as a fundamental wave can be observed.

From continuous observation of the harmonic components, it has been found that ratios of the harmonic components significantly change when a person is surprised, in a comfortable state, tensed, and the like.

For example, in a situation where a lie is pointed out in some game, or an attraction such as a roller coaster or a haunted house in an amusement park, the heart beat may beat fast due to being "startled". This fast beat due to being "startled" appears in the harmonic components of heartbeat.

It is therefore possible to estimate a human emotion and mental state by acquiring the harmonic components of the heartbeat and classifying and analyzing the ratios of the components according to emotions and states, without using brain waves.

[Emotion Estimating Apparatus: Schematic and External Views]

Figure 1A:
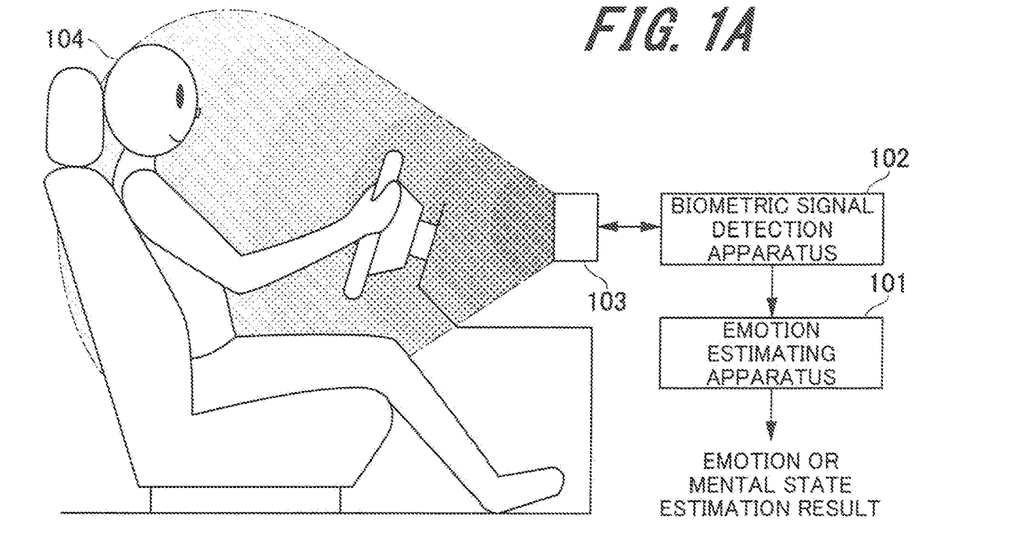
FIG. 1 is an external view of an emotion estimating apparatus according to an embodiment of the present invention.

FIG. 1A is a schematic view of an emotion estimating apparatus 101 mounted on a passenger car.

A biometric signal detection apparatus 102 radiates a radio wave from an antenna 103 to a driver 104 and receives a reflected wave of the radio wave. Then, predetermined signal processing is performed using the radiated wave and the reflected wave, whereby a pulse signal of the driver 104 is detected. The technology of the biometric signal detection apparatus 102 has already been devised by the present inventor (see Patent Literature 2).

When receiving a biometric signal from the biometric signal detection apparatus 102, the emotion estimating apparatus 101 internally performs A/D conversion and data processing described later, and estimates an emotion and mental state of the driver 104.

Emotion estimating result information output by the emotion estimating apparatus 101 is transmitted to a drowsy driving prevention system (not illustrated) mounted on the passenger car similarly to the emotion estimating apparatus 101 and is integrated with other information, and a state of the driver 104 is comprehensively determined. When it is determined as necessary, the drowsy driving prevention system carries out measures such as issuing a warning to the driver 104.

Figure 1B:
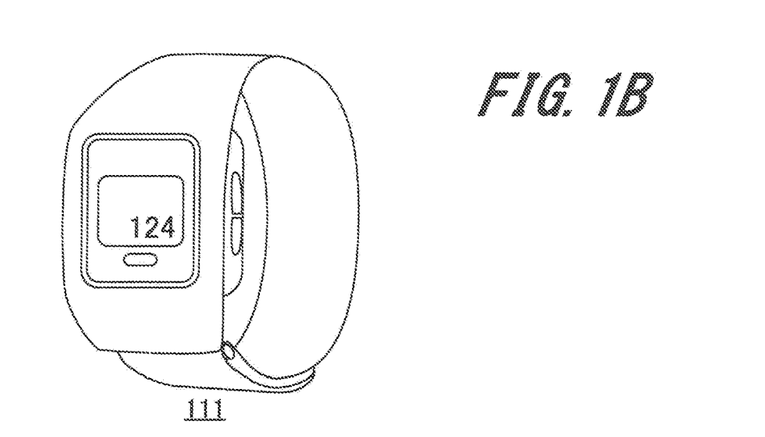

FIG. 1B is an external view illustrating an example of a pulse measurement apparatus 111 having a form of a wristwatch.

Figure 1C:
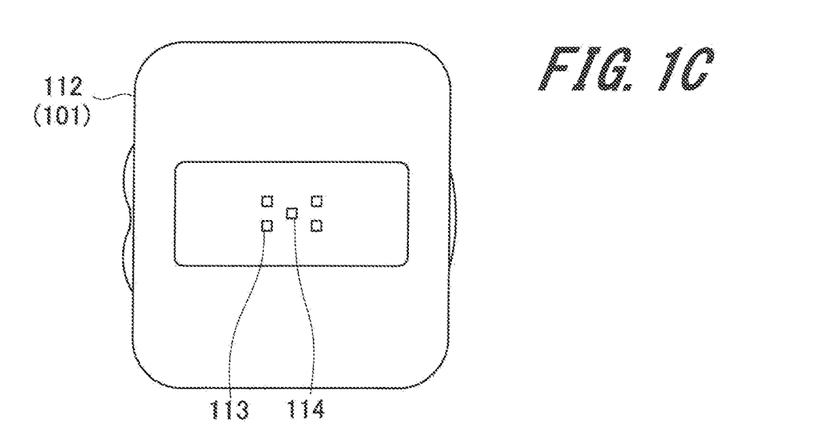

FIG. 1C is an external view illustrating the back side of the pulse measurement apparatus 111 having the form of the wristwatch.

In recent years, the pulse measurement apparatus 111 of a wristwatch-type has become widespread in the market. The pulse measurement apparatus 111 is provided with LED 113 that emits green light and a light receiving element 114, on the back side of a main unit 112 in the form of the wristwatch, and detects a change in light receiving intensity caused by a blood flow as a pulse signal. The principle of operation is similar to that of a pulse oximeter attached to an earlobe. That is, the pulse measurement apparatus 111 is a kind of biometric signal detection apparatus. It is therefore also possible to incorporate the emotion estimating apparatus 101 according to the embodiment of the present invention into the pulse measurement apparatus 111 of the wristwatch-type.

[Emotion Estimating Apparatus 101: Hardware Configuration]

Figure 2:
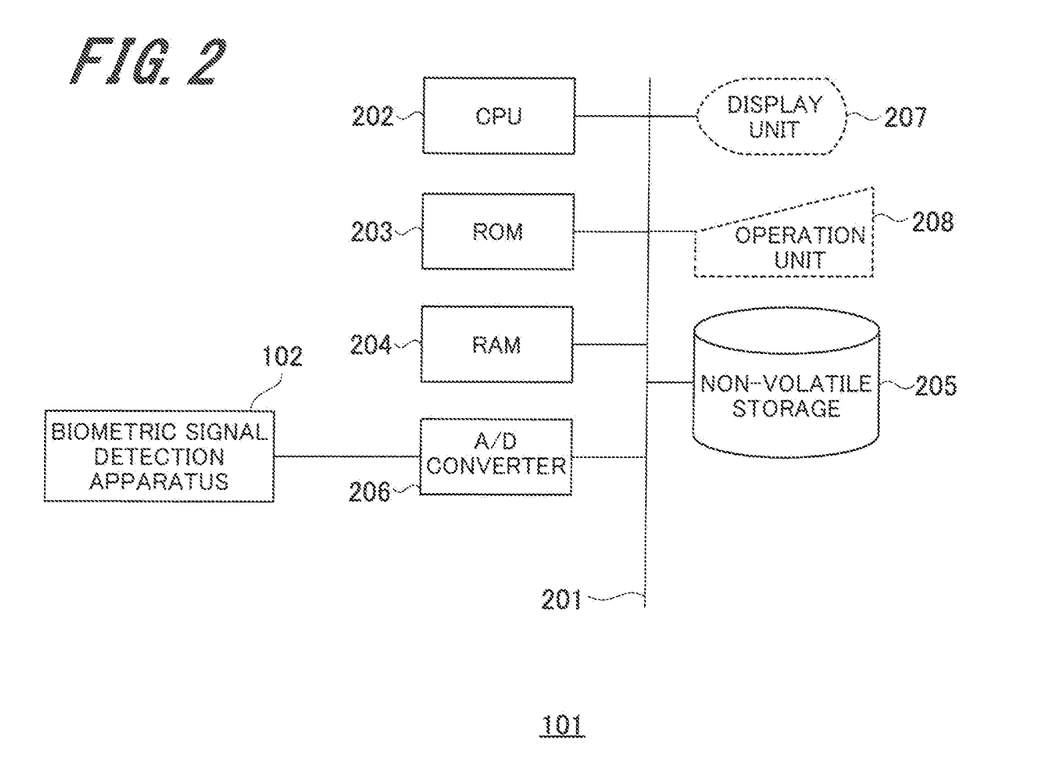
FIG. 2 is a block diagram illustrating a hardware configuration of the emotion estimating apparatus.

FIG. 2 is a block diagram illustrating a hardware configuration of the emotion estimating apparatus 101.

The emotion estimating apparatus 101 including a computer such as a one-board microcomputer includes a CPU 202, a ROM 203, a RAM 204, and a non-volatile storage 205 connected to a bus 201. As the non-volatile storage 205, a flash memory is used, for example. The flash memory can also be used as the ROM 203.

Further, the biometric signal detection apparatus 102 is connected to the bus 201 through an A/D converter 206. That is, an analog biometric signal output by the biometric signal detection apparatus 102 is converted into digital biometric data by the A/D converter 206. However, in a case where digital biometric data obtained by digitizing an analog biometric signal is directly output from the biometric signal detection apparatus 102, the A/D converter 206 is unnecessary.

Note that, depending on the form of the emotion estimating apparatus 101, it is also possible to connect a display unit 207 and an operation unit 208 to the bus 201 and present a user with an estimation result of the emotion or mental state.

As described above, the emotion estimating apparatus 101 can be implemented by a general microcomputer. The entity of the emotion estimating apparatus 101 is an information processing function provided by a program. A program function of the emotion estimating apparatus 101 can therefore also be bundled with software of a microcomputer constituting a part of the biometric signal detection apparatus 102, and configured integrally with the biometric signal detection apparatus 102.

[Emotion Estimating Apparatus 101: Software Function]

Figure 3:
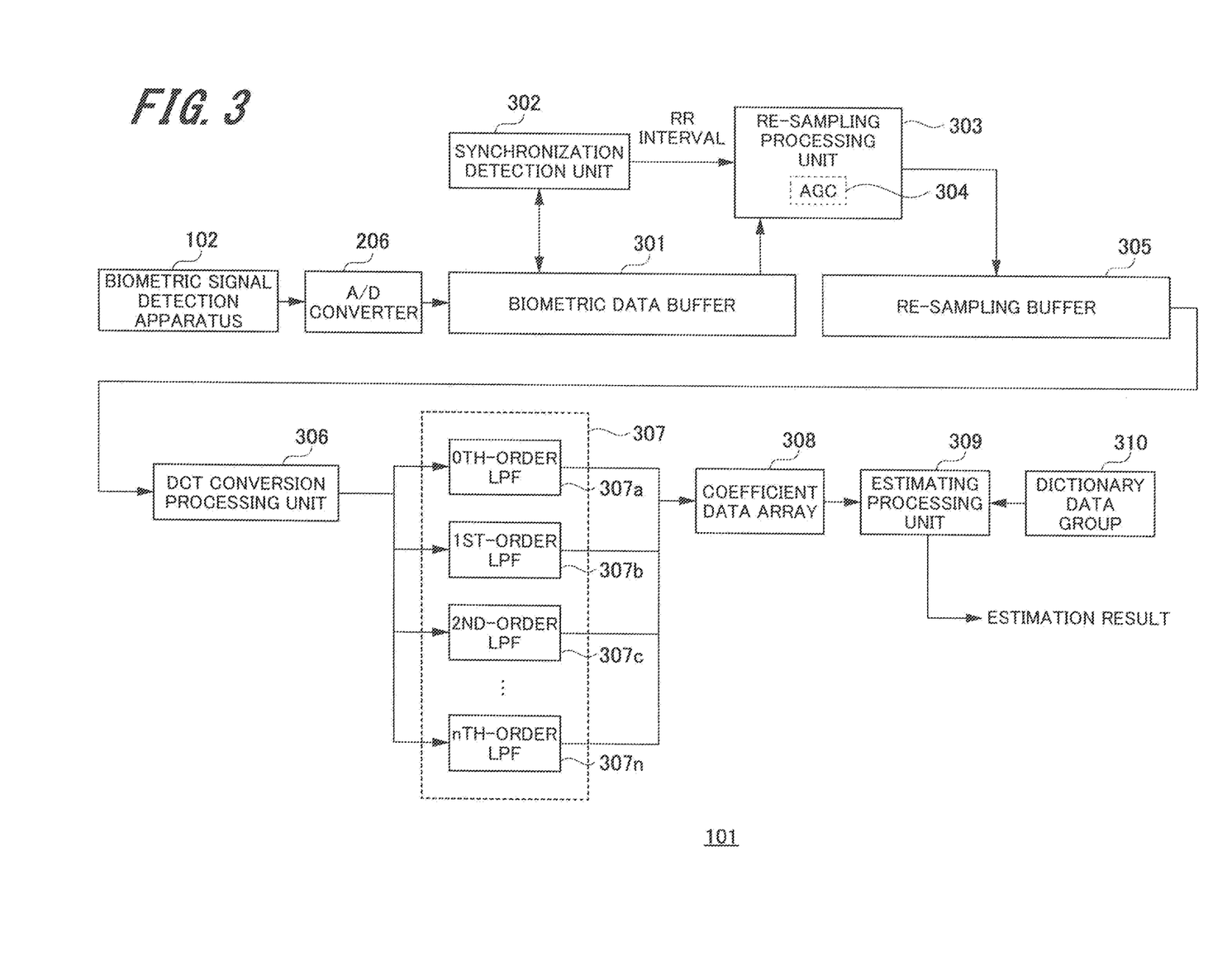
FIG. 3 is a block diagram illustrating software functions of the emotion estimating apparatus

FIG. 3 is a block diagram illustrating software functions of the emotion estimating apparatus 101.

The analog biometric signal output from the biometric signal detection apparatus 102 is converted into digital biometric data by the A/D converter 206. The digital biometric data is temporarily stored in a biometric data buffer 301. The biometric data buffer 101 has a storage capacity for storing the digital biometric data of at least two cycles or more.

A synchronization detection unit 302 reads the digital biometric data stored in the biometric data buffer 301, and detects the digital biometric data, that is, the R wave that is the peak of pulse data. Then, the RR interval indicating one cycle of the heartbeat is detected.

The RR interval information detected by the synchronization detection unit 302 is input to a re-sampling processing unit 303. The re-sampling processing unit 303 reads the RR interval information and the biometric data buffer 301, and performs, on the digital biometric data of one cycle, resampling processing and normalization processing by auto gain control (hereinafter "AGC") 304.

The cycle of the human pulse varies depending on factors such as health condition and activity condition. The re-sampling processing unit 303 forcibly applies one cycle of digital biometric data having variation to data of a certain number of samples, and writes the data to a re-sampling buffer 305, The number of samples of the re-sampling buffer 305 is preferably a power of two for the convenience of a DCT conversion processing 306 described later. The number of samples is, for example, 256 samples, 512 samples, or 1024 samples.

In addition, the amplitude of the analog biometric signal output from the biometric signal detection apparatus 102 is not necessarily normalized. In particular, in the case of the non-contact biometric signal detection apparatus 102 using a radio wave, the amplitude of the analog biometric signal may fluctuate depending on a transmission/reception environment of the radio wave. Thus, by having a function of the AGC 304 inside the re-sampling processing unit 303, the data stored in the re-sampling buffer 305 is normalized with respect to the amplitude, and it is enabled to obtain a correct harmonic component intensity in the DCT conversion processing unit 306 described later.

Normalized digital biometric data stored in the re-sampling buffer 305 is read into the DCT conversion processing unit 306, The DCT conversion processing unfit 306 performs known discrete cosine transform, and outputs a coefficient data array equal to the number of samples of the re-sampling buffer 305.

By the way, the harmonic components are frequency components of integral multiples of the fundamental wave. In other words, frequency components other than frequency components of integral multiples of the fundamental wave are not the harmonic components but noises. A low pass filter (hereinafter referred to as "LPF") is therefore provided for each coefficient in the coefficient data array output from the DOT conversion processing unit 306.

Coefficient data of the fundamental wave is input to a zeroth-order LPF 307a, coefficient data of the first-order harmonic is input to a first-order LPF 307b, coefficient data of the second-order harmonic is input to a second-order LPF 307c, . . . , and coefficient data of the nth-order harmonic is input to an nth-order LPF 307n, Hereinafter, when collectively referred to, the zeroth-order LPF 307a, the first-order LPF 307b, the second-order LPF 307c, . . . , and the nth-order LPF 307n are referred to as an LPF group 307. A cutoff frequency of each of the LPFs (low pass filter group) constituting the LPF group 307 is about 0.1 Hz.

A coefficient data array 308 thus obtained through each LPF of the LPF group 307 is estimated which coefficient data pattern included in a dictionary data group 310 is the closest by an estimating processing unit 309.

The dictionary data group 310 includes a plurality of coefficient data patterns related to various emotions and mental states of a subject to be measured. The patterns are, for example, elation, discomfort, fear, fatigue state, and the like.

The coefficient data array is a one-dimensional number sequence. To estimate a similarity between one-dimensional number sequences having the same number of elements, for example, calculation of residual sum of squares, or the like may be mentioned.

The estimating processing unit 309 calculates the similarity for each coefficient data pattern of the dictionary data group 310 for the coefficient data array 308, and outputs, as an estimation result, an emotion and mental state related to the coefficient data pattern whose similarity is the highest (distance between number sequences is the shortest).

[Emotion Estimating Apparatus 101: Operation]

As described above, in. the emotion estimating apparatus 101 according to the embodiment of the present. invention, the technology of acquiring the harmonic components of the heartbeat and capturing characteristics thereof is an important element technology. The inventor has therefore considered how to acquire the harmonic components of the heartbeat with high accuracy.

As described above, in the non-contact heartbeat detection technology, there is a large amount of noise components. In the first place, the heartbeat has fluctuation components, and the heartbeat becomes faster or slower due to biological activity.

However, the harmonic components of the heartbeat are frequencies of integral multiples of a fundamental wave component (RR interval) of the heartbeat. In other words, all frequency components that are not integral multiples of the fundamental wave component may be discarded as noises. Since fluctuation is also noise, components of this fluctuation can be removed first by normalization processing.

First, the re-sampling processing unit 303 performs synchronization detection on the RR intervals of pulse signals of a plurality of cycles. Then, re-sampling is forcibly performed every cycle, No matter how fast the pulse is or how slow the pulse is, in any case, sample values of the pulse cycle are forcibly equalized. Then, the number of sample values of all pulse cycles is equalized. The number of samples is, for example, 256 samples, The heartbeat cycles are forcibly equal) zed by the re-sampling processing unit 303, whereby the fluctuation components as noises are removed from the pulse. Then, the harmonic components included. in a pulse sample appear more clearly.

Next, the pulse sample subjected to noise removal is supplied to the DOT conversion processing unit 306, where discrete cosine transform (DOT) is performed. For example, when DOT is applied to the pulse samples of 256 samples, the coefficient data array 308 of the same number of samples (256) is obtained. The zeroth order is the fundamental wave, and subsequently, the first order is the second harmonic, the second order is the third harmonic, . . . , and the 255th order is the 256th harmonic.

Since the fluctuation components should have been removed by the re-sampling processing unit 303, the harmonic components output from the DOT conversion processing unit 306 appear as DC components, In other words, AC components that are not the DC components are noises. Thus, to these components, the LPFs for removing fluctuation components are applied. In this way, the coefficient data array 308 corresponding to the harmonic components of the pulse is obtained through the LPF group 307. By the above processing, subtle harmonic components included in the biometric signal appear clearly.

The inventor compares this coefficient data array 308 with a speech format and calls it a biological format.

That is, the emotion estimating apparatus 101 according to the embodiment of the present invention focuses on the harmonic components of the heartbeat that has not been noticed at all so far, and extracts the harmonic components. In a process of extracting the harmonic components, fluctuation components of the heartbeat to be detected in a conventional technology are completely ignored and removed as noises that interfere with detection of the harmonic components.

[Experimental Result]

Figure 4:
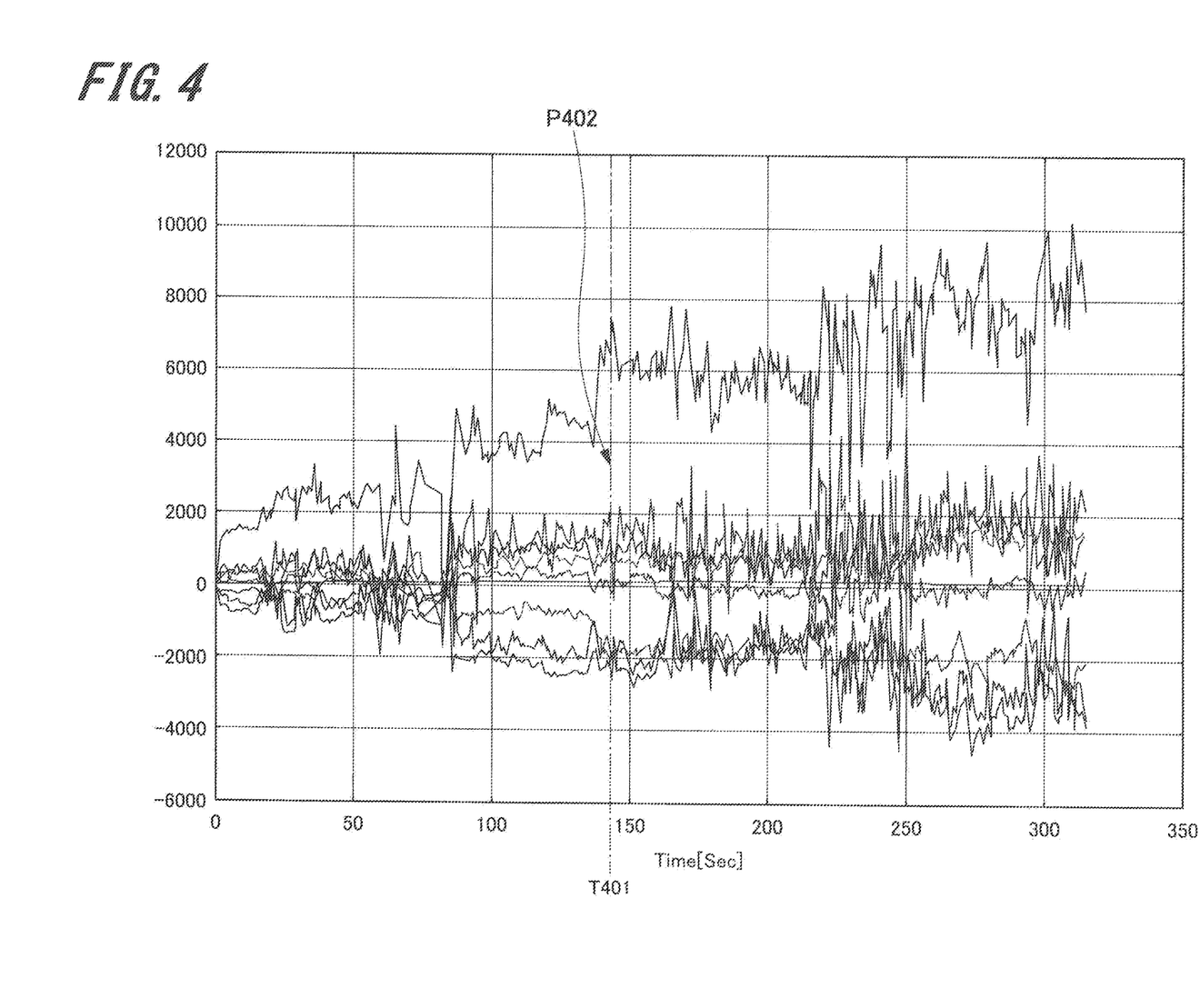
FIG. 4 is a graph illustrating changes in heart rate and harmonic components of heartbeat when a subject experiences a haunted house in an amusement park.

Fig, 4 is a graph illustrating changes in heart rate and harmonic components of heartbeat when a subject experiences a haunted house in an amusement park, The horizontal axis indicates the time, and the vertical axis indicates the magnitude of the harmonic component.

In the graph of FIG. 4, it is seen that, at time T401 when. the subject encountered a ghost in the haunted house, the subject's heartbeat value rises rapidly, and a significant change occurs in the eighth-order harmonic of the heartbeat (waveform P402).

Figure 5:
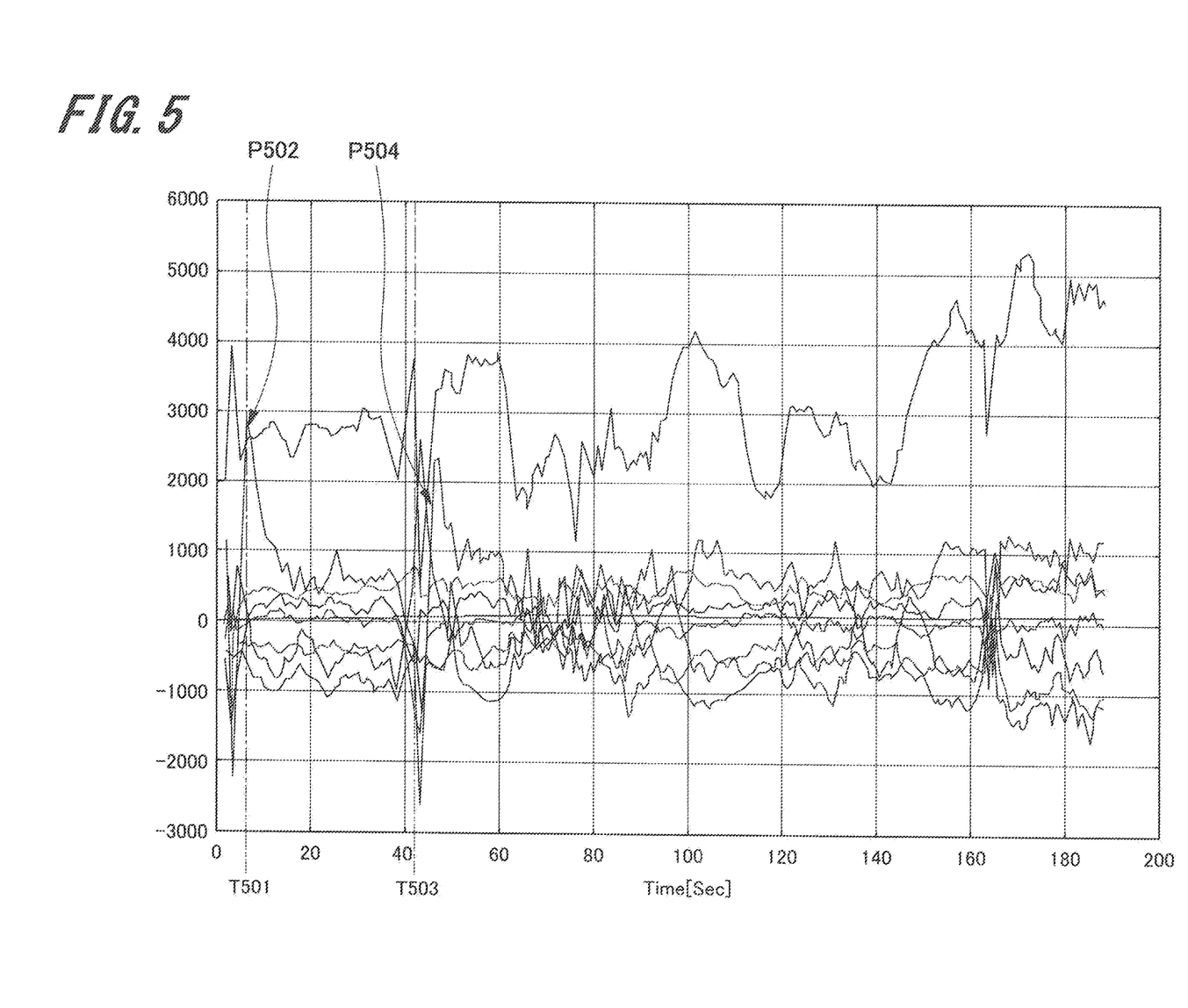
FIG. 5 is a graph illustrating changes in heart rate and harmonic components of heartbeat when another subject experiences a free fall in the amusement park.

FIG. 5 is a graph illustrating changes in heart rate and harmonic components of heartbeat when another subject experiences a free fall in the amusement park.

In the graph of FIG. 5, a state can be clearly seen in which the eighth-order harmonic of the subject's heartbeat rises rapidly when a ride part on which the subject is placed starts to move (time T501, waveform P502). It is seen that, thereafter, the eighth-order harmonic of the subject's heartbeat is gradually decreased along with a slow rise to the top of the tower. It is considered that, the subject feels surprise at the same time when the ride part first starts to move, and then an emotion of surprise is decreased as the ride part continues to rise.

Then, when the ride part starts to fall, a rapid change in emotion occurs in a short time (time T503). Although discrimination is difficult in FIG. 5, specifically, the first-order harmonic, the third-order harmonic, and the eighth-order harmonic rapidly decrease, and the second-order harmonic, the fourth-order harmonic, and the fifth-order harmonic rapidly increase. Next, the eighth-order harmonic increases rapidly (waveform P504). It is presumed that this increase is that the subject feels a feeling of exhilaration.

As illustrated in FIGS. 4 and. 5, it is seen that the harmonic components of the heartbeat cause a significant change with respect to fluctuation of a human emotion and mental state. Thus, these data are collected a lot, and classified for each emotion. Then, a plurality of the coefficient data arrays 308 related to the same emotion and mental state are prepared, and the plurality of coefficient data arrays 308 is subjected to arithmetic processing such as a least square method, to create dictionary data.

The estimating processing unit 309 calculates a distance between a plurality of dictionary data arrays included in the dictionary data group 310 with respect to a certain coefficient data array 308. The emotion or mental state related to dictionary data having the smallest value among the calculated distances is an estimation result of the emotion or mental state.

The estimating processing unit 309 can apply various estimation algorithms such as multiple regression analysis, principal component analysis, Bayesian estimation, support vector machine, and the like.

In each embodiment of the present invention, the emotion estimating apparatus 101 is disclosed.

The emotion estimating apparatus 101 forcibly performs re-sampling processing of the digital biometric data generated by converting a heart rate signal to digital data after extracting data for one cycle at the RR interval, and obtains coefficients of the harmonic components by the DCT conversion processing unit 306. Then, from the coefficients of the harmonic components, the AC components are removed by the LPFs, whereby the coefficient data array 308 is obtained. The coefficient data array 308 is compared to the dictionary data group 310, in which dictionary data is a characteristic quantity indicating an emotion or mental state, and a similarity therebetween is calculated, whereby an emotion or mental state of the subject is estimated on the basis of the heart rate signal of the subject.

By using the emotion estimating apparatus 101 according to each embodiment of the present invention, it is possible to implement detection and the like of a driver's near-miss in a passenger car without contact.

The embodiment of the present invention has been described above; however, the present invention is not limited to the above-described embodiment, and includes other modifications and application examples without departing from the gist of the present invention described in the claims For example, the above-described embodiment is a detailed and specific description of the configuration of the apparatus and system to explain the present invention. in an easy-to-understand manner, and is not necessarily limited to one having all the configurations described, In addition, it is also possible to replace part of the configuration of one embodiment with the configuration of another embodiment, and further, it is also possible to add, to the configuration. of one embodiment, the configuration of another embodiment. In addition, for part of the configuration of each embodiment, it is also possible to add, delete, and replace another configuration.

In addition, each configuration, function, processing unit, or the like described above may be implemented by hardware, for example, by designing part or all of them with an integrated circuit. In addition, each configuration, function, or the like described above may be implemented by software for a processor to interpret and execute a program that implements each function. Information such as programs, tables, and files that implement each function can be stored in a volatile or nonvolatile storage such as a memory, a hard disk, or a solid state drive (SSD), or a recording medium such as an IC card or an optical disk.

In addition, control lines and information lines indicate what is considered to be necessary for the description, and not all control lines and information lines in a product are necessarily indicated. In practice, almost all configurations may be considered to be connected to each other.

REFERENCE SIGNS LIST

101 Emotion estimating apparatus
102 Biometric signal detection apparatus
103 Antenna
104 Driver
111 Pulse measurement apparatus
112 Main unit
113 LED
114 Light receiving element
201 Bus
202 CPU
203 ROM
204 RAM
205 Non-volatile storage
206 A/D converter
207 Display unit
208 Operation unit
301 Biometric data buffer
302 Synchronization detection unit
303 Re-sampling processing unit
304 AGC
305 Re-sampling buffer
306 DCT conversion processing unit
307 LPF group
308 Coefficient data array
309 Estimating processing unit
310 Dictionary data group

The invention claimed is:

1. An emotion estimating apparatus comprising:
a re-sampling processing unit that extracts data for one cycle based on an RR interval from digital biometric data converted from a heart rate signal to digital data and converts the data to a predetermined number of samples;
a DCT conversion processing unit that performs discrete cosine transform on normalized digital biometric data whose number of samples is fixed by the re-sampling processing unit;
a low pass filter group that reduces an AC component for each coefficient data for a coefficient data array output from the DCT conversion processing unit; and
an estimating processing unit that estimates a most similar emotion or mental state by comparing the coefficient data array obtained from the low pass filter group with a dictionary data group that is an aggregation of dictionary data created for each emotion. or mental state.

2. The emotion estimating apparatus according to claim 1, wherein
the re-sampling processing unit performs auto gain control on the data for one cycle extracted from the digital biometric data on a basis of a peak value of an R wave.

\* \* \* \* \*